United States Patent [19]

Bauer et al.

[11] Patent Number: 4,923,887
[45] Date of Patent: May 8, 1990

[54] LIQUID FORMULATIONS OF 1,2-BENZISOTHIAZOLIN-3-ONE, THEIR PREPARATION AND THEIR USE

[75] Inventors: Wolfgang Bauer, Maintal; Hans-Walter Bücking, Kelkheim; Karl-Heinz Wallhäusser, Hofheim, all of Fed. Rep. of Germany

[73] Assignee: Cassella Aktiengesellschaft, Frankfurt am Main, Fed. Rep. of Germany

[21] Appl. No.: 236,903

[22] Filed: Aug. 25, 1988

Related U.S. Application Data

[63] Continuation-in-part of Ser. No. 19,520, Feb. 26, 1987, abandoned.

[30] Foreign Application Priority Data

Mar. 24, 1986 [DE] Fed. Rep. of Germany ....... 3609939

[51] Int. Cl.$^5$ .................... A61K 31/425; A61K 31/33
[52] U.S. Cl. .................... 514/373; 514/668; 514/669; 514/670
[58] Field of Search ............. 514/373, 668, 669, 670

[56] References Cited

U.S. PATENT DOCUMENTS 2,541,678  2/1951  Swaney et al. .................. 514/668
3,065,123  11/1962 Hinton et al. ................... 514/373
4,466,973  8/1984  Magami et al. .................. 514/373

FOREIGN PATENT DOCUMENTS 2302106  9/1976  France .......................... 514/669

OTHER PUBLICATIONS

Lion (I) CA. 96 #87465j (1982).
Lion (II) Ca. 103 #197718g (1985).

Primary Examiner—Allen J. Robinson
Assistant Examiner—Zohreh A. Fay
Attorney, Agent, or Firm—Connolly and Hutz

[57] ABSTRACT

Antimicrobially active liquid composition formulation which comprises 1,2-benzisothiazolin-3-one and at least one amine-oxyethylate of the formula

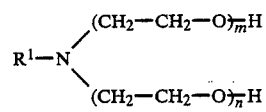

wherein R is alkyl or alkenyl each having 2 to 22 carbon atoms and the sum of m and n is a number from 2 to 30 is used as an improved biocide to preserve and protect aqueous solutions from infestation with micro-organisms.

4 Claims, No Drawings

LIQUID FORMULATIONS OF 1,2-BENZISOTHIAZOLIN-3-ONE, THEIR PREPARATION AND THEIR USE

This is a continuation-in-part of application serial no. 019,520 filed Feb. 26, 1987 now abandoned.

The present invention relates to new antimicrobially active liquid formulations of 1,2-benzisothiazolin-3-one of the formula I with one or more amine-oxyethylates of the formula II

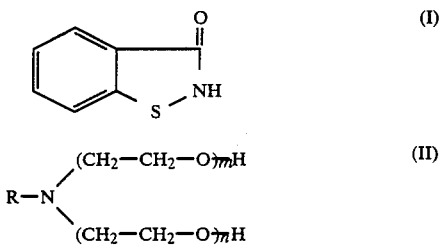

wherein R denotes alkyl or alkenyl with 8–22 C atoms and m +n denotes 2 to 30, and to their preparation and their use as industrial preservatives.

On the basis of its bactericidal and fungicidal properties, 1,2-benzisothiazolin in-3-one is used in industry as a biocide for protecting aqueous media against infections by microorganisms. For this intended use, it is desirable for the 1,2-benzisothiazolin-3-one to be in the form of a liquid formulation.

To prepare liquid formulations of 1,2-benzisothiazolin-3-one, it is already known that crude 1,2-benzisothiazolin-3-one obtained during synthesis can be used in the form of an aqueous dispersion. Such aqueous dispersions are not stable on storage, however, since settling occurs when they are left to stand.

Efforts have therefore been made to convert the crude 1,2-benzisothiazolin-3-one obtained during synthesis into liquid formulations which have the maximum possible concentration and at the same time are stable. According to British Patent Specification No. 1,191,253, one solution to this problem is to prepare aqueous solutions of crude 1,2-benzisothiazolin-3-one which contain two or more different amines selected from the series comprising diethanolamine, triethanolamine, diisopropanolamine, triisopropanolamine and morpholine. The 1,2-benzisothiazolin-3-one is present in these aqueous solutions as a mixture of the amine salts.

According to British Patent Specification No. 1,330,531, solutions of crude 1,2-benzisothiazolin-3-one in aliphatic, cycloaliphatic or heterocyclic amines which contain 2 to 6 C atoms and are free from hydroxyl and ether groups are prepared.

It has now been found, surprisingly, that the formulations, according to the invention, of 1,2-benzisothiazolin-3-one of the formula I with one or more amine-oxyethylates of the formula II display synergistic effects and have a clearly superior biological activity to the pure components I and II and the combinations of 1,2-benzisothiazolin-3-one with hydroxyethylamines described in British Patent Specification No. 1,191,253.

The liquid formulations according to the invention contain 1,2-benzisothiazolin-3-one and one or more amine-oxyethylates of the formula II. They consist of 1,2-benzisothiazolin-3-one and one or more amine-oxyethylates of the formula II, it also being possible for some of the amine-oxyethylate of the formula II to be replaced by water and/or one or more water-miscible organic solvents and/or one or more auxiliaries and/or complexing agents and/or water softeners.

If the liquid formulations according to the invention consist only of 1,2-benzisothiazolin-3-one of the formula I and of one or more amine-oxyethylates of the formula II, they usually contain 3 to 25% by weight, preferably 5 to 15% by weight, of 1,2-benzisothiazolin-3-one of the formula I and 97 to 75% by weight, preferably 95 to 85% by weight, of one or more amine-oxyethylates of the formula II.

For reasons of cost alone, it is as a rule advantageous to replace some of the amine-oxyethylate of the formula II by water and/or one or more water-miscible organic solvents. In order to be able to replace the maximum possible amount of amine-oxyethylate in the manner mentioned whilst retaining the required use properties, in particular the required storage stability, the composition of such liquid formulations according to the invention is advantageously chosen as follows: 3 to 25% by weight of 1,2-benzisothiazolin-3-one, 5 to 50% by weight of one or more amine-oxyethylates of the formula II, at least 10% by weight of one or more water-miscible organic solvents, 0 to 55% by weight of water, 0 to 15% by weight of one or more auxiliaries and 0 to 5% by weight of one or more complexing agents and/or water softeners.

The upper limit of the percentage content of the organic solvent or solvent mixture is the difference to make up to 100%.

The total of 1,2-benzisothiazolin-3-one and amine-oxyethylate in such formulations is advantageously 8 to 60% by weight, and/or the weight ratio of organic solvent or solvent mixture to water is advantageously 1 : (0 to 6), and especially preferably 1 : (0.8 to 5).

In liquid fOrmulations according to the invention which contain one or more water-miscible organic solvents, the composition is preferably 5 to 15% by weight of 1,2-benzisothiazolin-3-one, 9 to 45% by weight of one or more amine-oxyethylates of the formula II, the sum of 1,2-benzisothiazolin-3-one and amine-oxyethylate preferably being 14 to 45% by weight, 20 to 55% by weight of water, 0 to 10% by weight of one or more auxiliaries, 0 to 1% by weight of one or more complexing agents and/or water softeners and 10 to 35% by weight of one or more water-miscible organic solvents.

The liquid formulations according to the invention are prepared in a manner which is known per se by combining or mixing the components, the organic solvent or solvent mixture and/or, if appropriate, the amine-oxyethylate of the formula II advantageously being taken initially and the other components then being mixed in. When water is added, the major proportion is usually added only at the end.

The 1,2-benzisothiazolin-3-one can be employed in the form of the crude product obtained during synthesis, that is to say, for example, in the form of a water-moist press-cake, or in the pure form.

The amine-oxyethylates of the formula II are preferably employed in the form of their commercially available technical mixtures. They are prepared by reaction of fatty amines of the formula $RNH_2$, for example (coconut alkyl)-amine, stearylamine, oleylamine or (tallow alkyl)-amine, with ethylene oxide, for example with degrees of ethoxylation (=n+m) of 2 to 30, and are mixtures in respect to the radial R. In the preferred compositions, the amine-oxyethylates of the formula II have a degree of oxyethylation ($=n+m$) of 2 to 10, and especially preferably of 2.

It is apparent from the foregoing that n is a number from 1 to 30, preferably 1 to 10, and especially preferably the number 1 or 2, whereas m denotes a number from 0 to 15, preferably 0 to 5, and especially preferably the number 0 or 1.

Possible water-miscible solvents are, for example: lower mono-, di- and trihydric alcohols, glycols, di- and polyglycols and ethers of glycols and di- and polyglycols, such as, for example, ethanol and i-propanol; and propane-1,2-diol, propane-1,3-diol, glycerol, butane-1,2,3-triol, butane-1,2,4-triol, ethylene glycol, diethylene glycol, triethylene glycol, polyethylene glycol, dipropylene glycol, ethylene glycol mono-methyl ether, ethylene glycol mono-ethyl ether, ethylene glycol mono-propyl ether, ethylene glycol mono-butyl ether, diethylene glycol mono-methyl ether, diethylene glycol mono-ethyl ether, diethylene glycol mono-propyl ether, diethylene glycol mono-butyl ether, diethylene glycol dimethyl ether and diethylene glycol diethyl ether.

The use of glycols, such as, for example, 1,2-propylene glycol, or polyglycols, such as, for example, triethylene glycol, is preferred. It is also possible for a mixture of different organic solvents to be present in the formulations according to the invention.

Depending on the field of use of the formulations according to the invention, it may be advantageous to add to them nonionic and/or anionic auxiliaries which are known per se, such as emulsifying auxiliaries, dispersing auxiliaries and/or surfactants. This measure may be necessary if acid or neutral pH values are established during use and dilution of the formulations according to the invention and a good fine distribution of the 1,2-benzisothiazolin-3-one partly precipitated at these pH values is desired. Auxiliaries which have a good biological degradability are preferred here. The amount of emulsifying and/or dispersing auxiliaries and/or surfactants added is usually not more than 15% by weight, preferably not more than 10% by weight, based on the formulation.

It can furthermore be advantageous to add a complexing agent which is known per se and/or a water softener for complexing polyvalent cations, such as calcium ions or magnesium ions. The amount of complexing agent and/or water softener added is usually not more than 5% by weight, preferably not more than 1% by weight, based on the formulation.

The formulation can of course also contain a mixture of different auxiliaries and/or a mixture of different complexing agents and/or water softeners.

The liquid formulations according to the invention are employed, in particular, as industrial preservatives and are used, inter alia, for example, for protecting or preserving dispersions of polystyrene, polyacrylate and/or polyvinyl acetate, paints, boring and cutting oils, adhesives, paper coating compositions, textile softeners, starch-based sizes, detergent bases, cleaning and polishing agents, spinning baths, leather finishes and silicone and bitumen emulsions and for the treatment of industrial effluents in papermaking or industrial cooling water.

The synergistic increase of the biological activity in the formulations according to the invention which was not predictable is also associated, above all, with ecological advantages, in addition to economic advantages, since the use concentration of the active compound of the formula I for the protection of materials from microbial attack can be significantly reduced.

Ethoxylated (coconut alkyl)-amine, oleylamine, stearylamine and (tallow alkyl)-amine with a degree of ethoxylation of 2 are particularly preferred as the amine-oxyethylates. Ethoxylated (coconut alkyl)-amines with a degree of ethoxylation of 2 are commercially available, for instance from Hoechst AG, Frankfurt/Main 80, Germany under the trade name ®Genamine-C-020. The coconut alkyl in such ethoxylated coconut alkyl amines is a mixture of alkyl groups having a chain length of $C_8$ to $C_{18}$.

Especially preferred according to the present invention is an antimicrobially active liquid composition formulation which is a boicide for preserving and protecting aqueous solutions from infestation with Escherichia coli and which contains (a) 14 to 45% by weight of a mixture of substantially equimolar amount of 1,2-benziothiazolin-3-one and an ethoxylated (coconut alkyl)-amine with a degree of ethoxylation of 2, (b) 10 to 35% by weight of one or more water-miscible organic
solvents, (c) 20 to 55% by weight of water, (d) 0 to 15%, preferably 0 to 10%, most preferably 0% by weight of one or more water-miscible organic solvents and (e) 0 to 5%, preferably 0 to 1%, most preferably 0% by weight of one or more complexing agents.

The mixture of substantially equimolar amounts of 1,2-benziothiazolin-3-one and an ethoxylated (coconut alkyl)-amine with a degree of ethoxylation of 2, which mixture is present in the especially preferred antimicrobially active liquid composition formulation in amounts of 14 to 45% by weight and contains the 1,2-benzisothiazolin-3-one and the ethoxylated (coconut alkyl)amine with a degree of ethoxylation of 2 in a weight ratio of about 1 : (1.95 to 2). The examples 1, 5 to 8, 13 and 14, which follow below, show this weight ratio between 1,2-benzisothiazolin-3-one and the ethoxylated (coconut alkyl)-amine with a degree of ethoxylation of 2 and hence the formulation of these examples contain a mixture of substantially equimolar amounts of 1,2-benzisothiazolin-3-one and the said ehtoxylation product.

The following are examples of emulsifying agents that can be present in the especially preferred liquid compositions: salts of sulfuric acid esters, such as Na-laurylsulfate, Na-salts of sulfosuccinic acid esters, sulfuric acid esters of ethoxylated fatty alcohols and alkylphenols; salts of sulfonic acids, such as alkylbenzenesulfonates, xylenesulfonates and naphthalinesulfonates, alkylnaphthalinesulfonates, alkanesulfonates, in particular alkanesulfonates having a chain length of $C_{12}$ to $C_{18}$; ethyleneoxide- and propyleneoxide adducts, for example with fatty acids, fatty alcohols, fatty amines, alkylphenols, partial fatty acid esters of polyhydric alcohols and of sorbitol; polyalkylene glycol. The following emulsifying agents are preferred: alkanesulfonates, in particular secondary alkanesulfonates having a chain length of $C_{12}$ to $C_{18}$, alkylphenol polyglycol ethers, in particular nonylphenol polyglycol ether, fatty alcohol polyglycol ethers, fatty acid polyglycol esters.

Complexing agents which can be present in the particularly preferred liquid composition formulations are in particular those based on ethylene diamino tetraacetic acid. Such complexing agents are marketed by, for example, Cassella AG, 6000 Frankfurt/Main 61 under the name ®Aquamollin.

The invention is illustrated in more detail by the following examples, the amine-oxyethylates being used in the form of ®Genamin commercial products from Hoechst AG, Frankfurt/Main 80. These ®Genamin commercial products are oxyethylates of fatty amines. The ®Genamin tradenames have an added letter C, S, O or T and a number. C means (coconut alkyl)-amine with an approximate average chain distribution of 6% of $C_8$, 6% of $C_{10}$, 54% of $C_{12}$, 18% of $C_{14}$, 8% of $C_{16}$ and 8% of $C_{18}$; S denotes stearylamine with an approximate average chain distribution of 5% of $C_{14}$, 30% of $C_{16}$ and 65% of $C_{18}$; O denotes oleylamine with an approximate average chain distribution of 1% of $C_{12}$, 4% of $C_{14}$, 12% of $C_{16}$ and 83% of $C_{18}$ and T denotes (tallow alkyl)-amine with an approximate average chain distribution of 5% of $C_{14}$, 30% of $C_{16}$ and 65% of $C_{18}$. The accompanying number, when divided by 10, gives the degree of ethoxylation. For example, ®Genamin C-020 is thus an ethoxylated (coconut alkyl)-amine with a degree of ethoxylation of 2.

Unless indicated otherwise, percentages denote percentages by weight.

EXAMPLE 1

132.5 g of a water-moist press-cake of crude 1,2-benzisothiazol-3-one (content 75.5%, remainder water) are introduced into a mixture of 300 g of 1,2-propylene glycol, 300 g of water and 195 g of ®Genamin C-020 at 40° C., with stirring. The weight is brought to 1 kg by addition of water and a liquid, storage-stable formulation containing 10% of 1,2-benzisothiazol-3-one, 19.5% of ®Genamin C-020 and 30% of 1,2-propylene glycol, the remainder being water, is obtained.

The formulations, according to the invention, in the following Examples 2 to 14 can be prepared in a manner analogous to that in Example 1.

EXAMPLE 2

10% of 1,2-benzisothiazolin-3-one, 28.4% of ®Genamin C-050, 20% of 1,2-propylene glycol and 41.6% of water.

EXAMPLE 3

10% of 1,2-benzisothiazolin-3-one, 42.6% of ®Genamin C-100, 20% of 1,2-propylene glycol and 27.4% of water.

EXAMPLE 4

5% of 1,2-benzisothiazolin-3-one, 37% of ®Genamin C-200, 10% of 1,2-propylene glycol and 48% of water.

EXAMPLE 5

10% of 1,2-benzisothiazolin-3-one, 19.5% of ®Genamin C-020, 10% of ®Hostapur SAS 93 (commercially available alkanesulphonate from Hoechst AG), 20% of 1,2-propylene glycol and 40.5% of water.

EXAMPLE 6

10% of 1,2-benzisothiazolin-3-one, 19.5% of ®Genamin C-020, 10% of ®Arkopal N 100 (commercially available nonylphenolpolyglycol ether from Hoechst AG), 20% of 1,2-propylene glycol and 40.5% of water.

EXAMPLE 7

10% of 1,2-benzisothiazolin-3-one, 19.5% of ®Genamin C-020, 10% of ®Genapol X 080 (commercially available fatty alcohol polyglycol ether from Hoechst AG), 20% of 1,2-propylene glycol and 40.5% of water.

EXAMPLE 8

10% of 1,2-benzisothiazolin-3-one, 19.5% of ®Genamin C-020, 2% of Emulsogen EL (commercially available emulsifier from Hoechst AG), 20% of 1,2-propylene glycol and 48.5% of water.

EXAMPLE 9

10% of 1,2-benzisothiazolin-3-one, 19.5% of ®Genamin C-020, 0.5% of ®Aquamollin BC (water softener from Cassella AG, Frankfurt/Main-Fechenheim), 20% of 1,2-propylene glycol and 50% of water.

EXAMPLE 10

10% of 1,2-benzisothiazolin-3-one, 17% of ®Genamin S-020, 30% of 1,2-propylene glycol and 43% of water.

EXAMPLE 11

10% of 1,2-benzisothiazolin-3-one, 20% of ®Genamin 0-020, 30% of Polydiol 400 (polyethylene glycol with an average molecular weight of 400) and 40% of water.

EXAMPLE 12

10% of 1,2-benzisothiazolin-3-one, 16% of ®Genamin T-020, 30% of triethylene glycol and 44% of water.

EXAMPLE 13

15% of 1,2-benzisothiazolin-3-one, 29.3% of ®Genamin C-020, 30% of dipropylene glycol and 25.7% of water.

EXAMPLE 14

5% of 1,2-benzisothiazolin-3-one, 9.8% of ®Genamin C-020, 10% of 1,2-propylene glycol, 2% of glycerol, 20% of isopropanol and 53.2% of water.

EXAMPLE 15

10 parts by weight of 1,2-benzisothiazolin-3-one are dissolved in 90 parts by weight of ®Genamin C-020, with stirring.

COMPARISON EXAMPLE WITH A FORMULATION WHICH IS NOT ACCORDING TO the invention 6.6 g of a water-moist press-cake of crude 1,2-benzisothiazolin-3-one (content 75.5%, remainder water) are dissolved in a mixture of 30 g of 1,2-propylene glycol, 50 g of water and 9.8 g of triethanolamine. The composition, when brought to 100 g with water, contains 5% of 1,2-benzisothiazolin-3-one, 9.8% of triethanolamine, 30% of 1,2-propylene glycol and 55.2% of water. (No aqueous formulation of higher concentration can be prepared, for solubility reasons).

TEST METHOD

Comparative testing is carried out in a series dilution test using a standardized casein peptin-soya peptin broth (CSB), such as is commercially available. The dilution stages ranged from 400 μg/ml, 200 μg/ml, 100 μg/ml to 6.26 μg/ml. After incubation of the bacteria and yeasts at 32° C., the inhibiting action (bacteristasis and fungistasis) was read off after 24 hours and the MIC (minimum inhibitory concentration) was stated in μg/ml. To determine the microbicidally active (destructive) concentration (μg/ml), all the small tubes which did not become cloudy in the series dilution test (no visible growth) were smeared onto malt agar slant tubes and incubated at 32° C. for 24 hours. That value at which no further growth was to be observed on the slant agar tubes was determined as the microbicidal concentration (in μg/ml). The following results were obtained:

| | Formulations | | | |
|---|---|---|---|---|
| | Example 1 | | Comparison Example | |
| Test organisms | Inhibition at μg/ml | Destruction at μg/ml | Inhibition at μg/ml | Destruction at μg/ml |
| Staph. aureus | <6.25 | 50 | | 200 |
| E. Coli | 12.5 | 25 | 200 | 200 |
| Ps. aeruginosa | 100 | 100 | >200 | >200 |
| Candida albicans | 25 | 25 | >200 | >200 |

What is claimed is:

1. Antimicrobially active liquid composition formulation which is a biocide for preserving and protecting aqueous solutions from infestation with Escherichia coli and which contains
   (a) 14 to 45% by weight of a mixture of substantially equimolar amounts of 1,2-benzisothiazolin-3-one and an ethoxylated (coconut alkyl)-amine with a degree of ethoxylation of 2;
   (b) 10 to 35% by weight of one or more water-miscible organic solvents, selected from the group consisting of lower mono-, di-and trihydric alcohols, glycols, di- and polyglycols, ethers of glycols and di- and polyglycols;
   (c) 20 to 55% by weight of water;
   (d) 0 to 15% by weight of one or more emulsifying agents, selected from the group consisting of sulfuric acid esters; salts of sulfonic acids; ethyleneoxide and propyleneoxide adducts with fatty acids, fatty alcohols, fatty amines, alkylphenoles, partial fatty acid esters of polyhydric alcohols and of sorbitol; and polyalkylene glycol; and
   (e) 0 to 5% by weight of one or more complexing agents based on ethylene diamino tetraacetic acid.

2. Antimicrobially active liquid composition formulation according to claim 1, wherein the coconut alkyl of the ethoxylated (coconut alkyl)-amine with a degree of ethoxylation of 2 is a mixture of alkyl groups with a chain length of $C_8$ to $C_{18}$.

3. Antimicrobially active liquid composition formulation which is a biocide for preserving and protecting aqueous solutions from infestation with Escherichia coli and which contains
   (a) 14 to 45% by weight of a mixture of substantially equimolar amounts of 1,2-benzisothiazolin-3-one and an ethoxylated (coconut alkyl)-amine with a degree of ethoxylation of 2;
   (b) 10 to 35% by weight of one or more water-miscible organic solvents, selected from the group consisting of lower mono-, di-and trihydric alcohols, glycols, di- and polyglycols, ethers of glycols and di- and polyglycols;
   (c) 20 to 55% by weight of water, selected from the group consisting of sulfuric acid esters; salts of sulfonic acids; ethyleneoxide and propyleneoxide adducts with fatty acids, fatty alcohols, fatty amines, alkylphenoles, partial fatty acid esters of polyhydric alcohols and of sorbitol; and polyalkylene glycol;
   (d) 0 to 10% by weight of one or more complexing agents based on ethylene diamino tetraacetic acid.

4. Antimicrobially active liquid composition formulation which is a biocide for preserving and protecting aqueous solutions from infestation with Escherichia coli and which contains
   (a) 14 to 45% by weight of a mixture of substantially equimolar amounts of 1,2-benzisothiazolin-3-one and an ethoxylated (coconut alkyl)-amine with a degree of ethoxylation of 2;
   (b) 10 to 35% by weight of one or more water-miscible organic solvents, selected from the group consisting of lower mono-, di-and trihydric alcohols, glycols, di- and polyglycols, ethers of glycols and di- and polyglycols; and
   (c) 20 to 55% by weight of water.

* * * * *